United States Patent [19]

Capone

[11] 4,169,769
[45] Oct. 2, 1979

[54] METHOD FOR CONVEYING A GAS SAMPLE THROUGH AN ANALYZER CHAMBER

[75] Inventor: David M. Capone, Oakmont, Pa.

[73] Assignee: Thermo-Lab Instruments, Inc., Pittsburgh, Pa.

[21] Appl. No.: 904,876

[22] Filed: May 11, 1978

Related U.S. Application Data

[62] Division of Ser. No. 739,712, Nov. 8, 1976, Pat. No. 4,115,235.

[51] Int. Cl.² ............................................. G01N 27/46
[52] U.S. Cl. ........................................ 204/1 T; 73/23
[58] Field of Search ................. 204/1 S, 1 T, 195 S, 204/195 R; 73/23, 27 R; 23/254 R, 254 E, 254 EF, 255 R, 255 E, 232 R, 232 E; 324/29

[56] References Cited

U.S. PATENT DOCUMENTS

| Re. 29,209 | 5/1977 | Sayles | 204/195 S |
|---|---|---|---|
| 1,504,707 | 8/1924 | Peters | 73/27 R |
| 1,874,549 | 8/1932 | Krueger et al. | 73/27 R |
| 2,807,159 | 9/1957 | Wilson | 73/27 R |
| 3,791,936 | 2/1974 | Pebler et al. | 204/1 S |
| 3,960,500 | 6/1976 | Ross et al. | 204/1 S |
| 4,115,229 | 9/1978 | Capone | 204/195 S |

*Primary Examiner*—T. Tung
*Attorney, Agent, or Firm*—Stanley J. Price, Jr.; John M. Adams

[57] ABSTRACT

A gas analyzer is provided which is comprised of two gas sample flow loops joined at an angle to each other, one being an eductive loop that originates and returns to the chamber or conduit from which a gas sample is to be drawn and the other being a convective loop that joins in fluid flow communication with the eductive loop at a point upstream from its eductor device.

5 Claims, 7 Drawing Figures

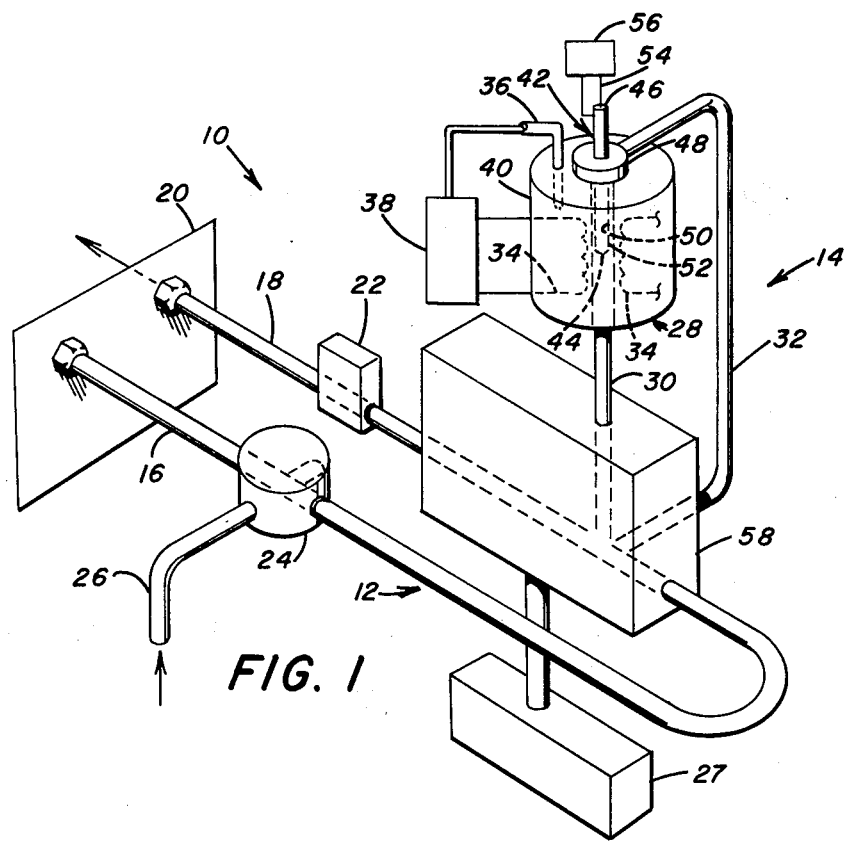
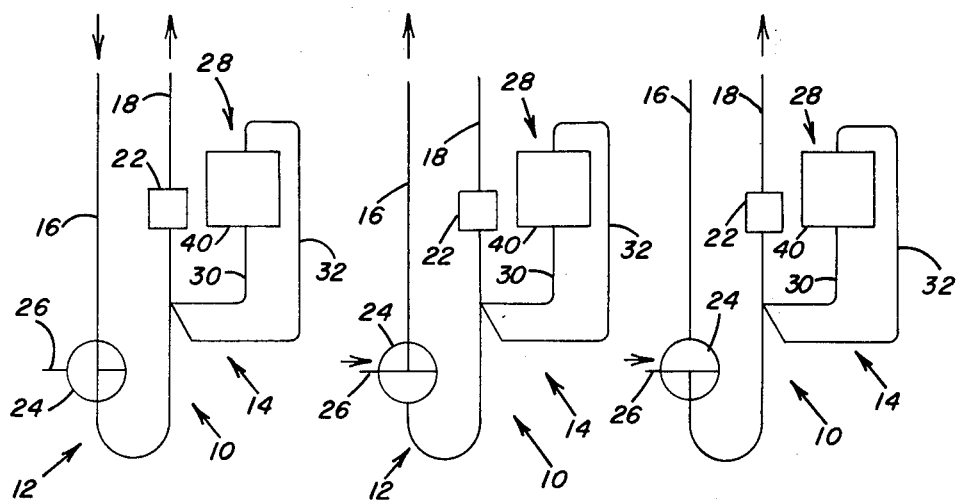
FIG. 1
FIG. 2A   FIG. 2B   FIG. 2C

METHOD FOR CONVEYING A GAS SAMPLE THROUGH AN ANALYZER CHAMBER

CROSS REFERENCES TO RELATED APPLICATIONS

This application is a division of copending application, Ser. No. 739,712 filed on Nov. 8, 1976, now U.S. Pat. No. 4,115,235 entitled "Method And Apparatus For Conveying A Gas Sample Through An Analyzer Chamber".

BACKGROUND OF THE INVENTION

1. Field of the Invention

This invention relates to a method and apparatus for sensing the condition of a gas and, more specifically, to a method and apparatus particularly suitable for analyzing gas in a chamber or conduit where the gas to be analyzed is highly vulnerable to substantial fluctuations in its pressure. As used in this specification the term "condition" or "condition of a gas" is intended to refer to either the physical or chemical or other properties of the gas being analyzed.

2. Description of the Prior Art

Gas analyzers that depend on aspirators or other eductor devices at their exit portion to move the gas sample through the instrument, particularly those using aspirators motivated by air or other gases, suffer from the disadvantage of being very unstable in their operation as the inlet pressure varies. If the motive-fluid pressure is adjusted to obtain the desired sample flow rate with one particular inlet pressure, then higher inlet pressures will cause an excessively high sample flow rate while lower inlet pressures (including vacuums) may result in inadequate sample flow, no flow or reversed flow.

Accordingly, there is a need for a method and apparatus for sensing the condition of a gas or gases in a chamber or flow path when the gas to be analyzed is susceptible to substantial fluctuations in its pressure.

SUMMARY OF THE INVENTION

In accordance with the present invention, there is provided a novel method and apparatus for analyzing a gas or gases subject to pressure variations. More specifically, there is provided a gas analyzer comprised of two gas sample flow loops, connected to each other, one being an eductive loop that originates and returns to the chamber or conduit from which a gas sample is to be drawn and the other, preferably, being a convective loop that joins in fluid flow communication with the eductive loop at a point upstream from its eductor device. In particular, a gas analyzer is disclosed having a flow path from the chamber or conduit containing the sample to be analyzed which then contains a bend that directs the sample back to the chamber or conduit from which it originated. An aspirator or eductor device is located in this flow loop downstream from the point at which a small portion of the sample may flow upwards by convection into a heated section containing the gas sensing element.

The foregoing and other objects, features and advantages of this invention will become more apparent when taken in conjunction with the following specification, the accompanying drawings and the appended claims.

BRIEF DESCRIPTION OF THE DRAWINGS

In the drawings, wherein like numerals are used to indicate like parts throughout the same:

FIG. 1 is a schematic representation of one embodiment of this invention;

FIGS. 2a, 2b and 2c are diagrammatic representations of the gas analyzer of FIG. 1 showing three operative positions of a valve controlling blowback air;

DESCRIPTION OF PREFERRED EMBODIMENTS

Figures 3, 4:
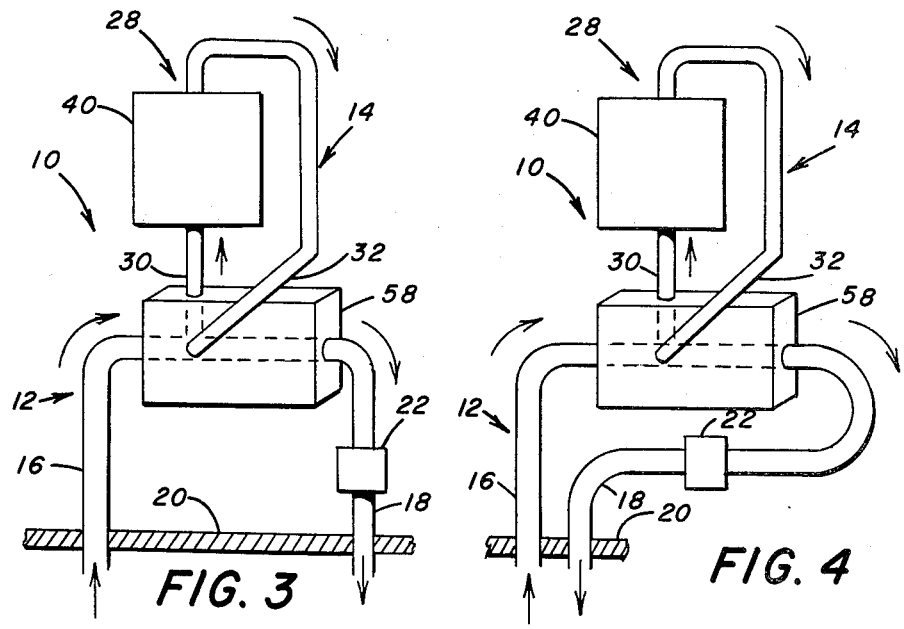
FIGS. 3 and 4 are schematic representations of an alternative arrangement of the device of this invention.

Referring to FIG. 1, there is shown a gas analyzer 10 of this invention in one preferred arrangement. Basically, in the embodiment shown, gas analyzer 10 is comprised of two flow loops, i.e., an eductive flow loop 12 and a convective flow loop 14.

Eductive flow loop 12 is essentially a continuous conduit having a 180° bend at its midportion to present two approximately parallel, open ends or legs, i.e., a sample inlet or leg 16 and a return end or leg 18, for attachment in a conventional manner in fluid flow communication with a side of chamber or conduit 20 containing the gas or gases to be sampled. Interposed along the length of eductive flow loop 12 is an eductor device 22 located at some point downstream of where convective flow loop 14 joins the eductive flow loop. Also, optionally interposed at some point upstream of both eductor device 22 and convective flow loop 14, is a rotary valve 24 and blowback air conduit 26 which may be useful, although not necessarily essential, in the practice of the invention. Furthermore, optionally attached at any convenient location, such as to junction block 58, there is schematically illustrated a vibrator or mechanical shaker or "rapper" 27 of any desired construction, pneumatic or otherwise, that may also be useful, although not necessarily essential in the practice of this invention. If used with this or any subsequent embodiment of this invention, it will be understood that it will function to prevent any particulate matter from building up on the interior wall of the sample flow conduits or plumbing circuit of analyzer 10, or to loosen such particulate matter if it does build up, due to imparting low amplitude, oscillatory motion to analyzer 10. Further, it may be useful, although not necessarily essential, to momentarily increase the sample flow in the eductive flow loop 12 to approximately coincide with said oscillatory motion to analyzer 10 thereby helping to move particulate matter thus suspended. This increase in sample flow may or may not be produced by increasing the flow of motive fluid to eductor 22.

As aforesaid, located at a point upstream of eductor device 22 is the convective flow loop 14. To provide a predictable continuous flow of gas past gas sensing device 28 a temperature differential is maintained between inlet leg 30 and outlet leg 32 of loop conduit 14 by heater element 34 positioned around inlet leg 30. The heater element 34 is controlled by means of a temperature sensor 36 such that the temperature in the inlet leg 30 is maintained at a preselected value, preferably in the range of about 600° F. to 1800° F., by means of a conventional temperature controller 38. An enclosure 40 houses the heater element 34 to confine the increased temperature to the inlet leg 30 and maintain the desired temperature differential between the inlet leg 30 and the outlet leg 32 of loop conduit 14. It will be apparent that with this arrangement the temperature of the inlet leg 30 of the loop conduit 14 will be maintained at a higher temperature than the outlet leg 32. Although a heater element is illustrated for maintaining this temperature differential, it will also be apparent that this temperature differential could be enhanced, or even independently maintained, by cooling the outlet leg 32 and thereby providing a temperature differential between the inlet leg 30 and the outlet leg 32 to obtain convective flow.

The sensing device 28 illustrated in the drawings is a ceramic oxide electrochemical cell that measures the oxygen partial pressure of the sample. The sensing device includes a tube 42 of ceramic oxide material having a closed end portion 44 and an open end portion 46. The tube is positioned in inlet leg 30 with the closed end portion facing into or toward the gas flow path and the open end of the tube extending beyond the seal 48. The inside of tube 42 is provided with a porous conductive electrode coating 50 and the outside of the tube is provided with a similar porous conductive electrode coating 52. The coatings or electrodes 50 and 52 are connected through a circuit 54 to a voltage measuring device 56 which is arranged to indicate the EMF produced by the electrochemical cell. Electrochemical cells for measuring oxygen partial pressure are well known and suitable cells for use with this invention and their mode of operation are disclosed in U.S. Pat. Nos. 3,597,345, 3,865,707 and 3,869,370, the disclosures of which are incorporated herein by reference.

In the operation of the novel analyzer of this invention, a sample of gas or gases to be analyzed is drawn from conduit or chamber 20 into inlet leg 16 of eductive loop 12 by means of eductor 22. As the drawn sample traverses the eductive loop 12, a small portion of the sample is drawn by convection into leg 30 of convective loop 14, which as shown, is in fluid flow communication with eductive loop 12 via junction block 58 positioned at a point or location upstream of eductor 22. With reference to the aforementioned U.S. patents it will be understood that, as this small portion of the sample flows past sensing element 28, the oxygen partial pressure is indicated by an electrical signal which is measured so as to provide, through appropriate logic circuitry, a direct reading of the excess oxygen or excess fuel contained in the sample. The sensed portion of the sample is then returned to eductive loop 12 via return leg 32 where it is permitted to be withdrawn from eductive loop 12 by downstream eductor 22 and returned to chamber or conduit 20 through leg 18. As will be understood, by reason of legs 16 and 18 having their openings in chamber 20 position at a location of the same or approximately the same chamber pressure, the rate of flow of sample through eductive loop 12 is unaffected or substantially unaffected by fluctuations in the chamber pressure. Thus, the desired rate of flow having been initially set by establishing the operating parameters of eductor 22, the analyzer 10 will provide a substantially continuous analysis of the desired conditions of the gas being sampled at substantially the same flow without requiring readjustment due to variations in chamber pressure.

Shown diagrammatically in FIGS 2a and 2c are suitable desired positions for valve 24. As will be understood, the position of valve 24 in FIG. 2a is that of the sample position. In FIG. 2b, however, the valve 24 has been rotated counterclockwise, as viewed, from its sample position to discontinue the flow of sample gas and to permit air entering under pressure through conduit 26 to flow back the portion of eductive flow loop 12 upstream of valve 24. Similarly, in FIG. 2c the valve 24 has been rotated clockwise from its sample position to discontinue the flow of sample and to permit blowback air entering under pressure through conduit 26 to blow back the portion of eductive flow loop downstream of valve 24. Such an arrangement is useful in the event a build-up of deposits could occur due to sampling dirty or wet gas or gases that would eventually cause plugging of the analyzer. Moreover, it will be understood that the disclosed vibrator or mechanical shaker or rapper 27 may be used in lieu of or in addition to the described blowback arrangement and that both are optional appurtenances, neither of which is essential to the practice of the invention.

Shown in FIGS. 3 and 4 is an arrangement of this invention that is useful when it is preferred to withdraw and return the sample to be analyzed from the top of a chamber or conduit 20. The essential difference between the embodiments of FIGS. 3 and 4, when compared to the embodiment of FIG. 1, is in the disposition or orientation of the eductive loop 12. In the embodiment of FIG. 1, the eductive loop 12 is arranged or extends generally horizontally of chamber or conduit 20, whereas, convective loop 14, for the purpose of aiding in convective flow, is arranged in a generally vertical disposition. In contradistinction, the embodiments of FIGS. 3 and 4 employ an essentially vertical eductive loop 12, for ease of attachment to the top of a chamber or conduit 20, in combination with an essentially vertical convective loop 14 extending upwardly therefrom. Notwithstanding, the necessary components of this invention, as shown in FIG. 1, are also illustrated as being present in FIGS. 3 and 4 and their function or mode of operation is the same as described in connection with FIG. 1.

Figure 5:
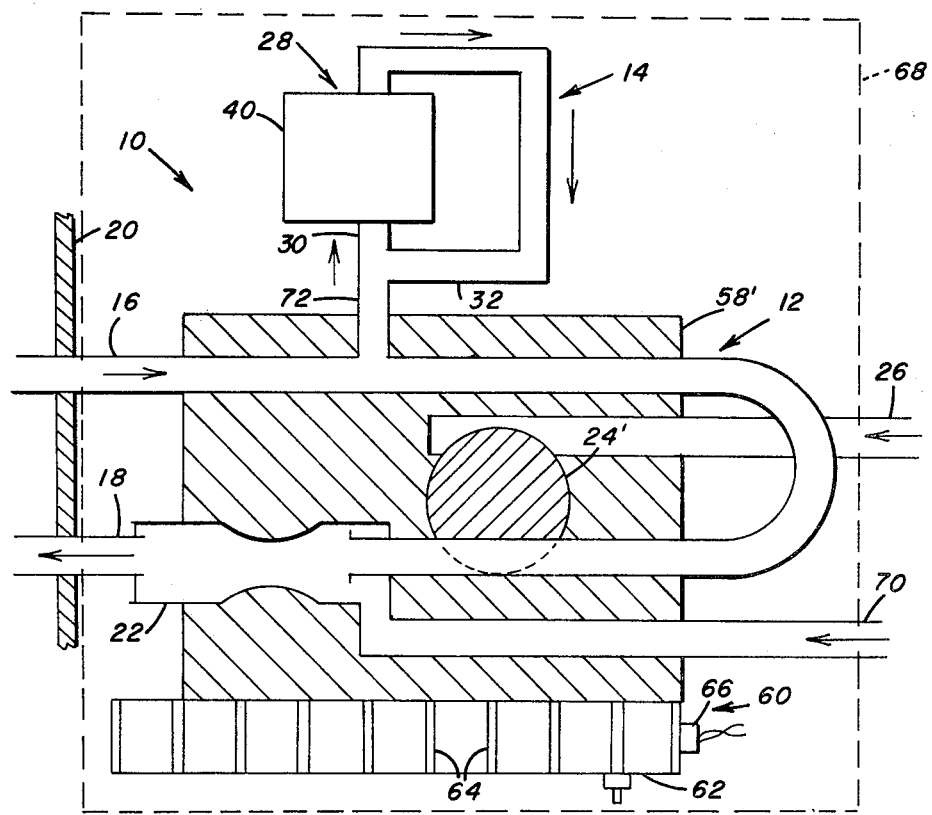
FIG. 5 is an enlarged schematic of a further embodiment of this invention.

In FIG. 5 there is shown another embodiment of this invention. Again, all of the necessary components of the invention are illustrated as being present and their function or mode of operation remains the same as aforesaid. Accordingly, the following description will be generally confined to the differences and/or additional details illustrated in FIG. 5 that do not appear in FIGS. 1 through 4.

A principal difference of the FIG. 5 construction, not previously illustrated, is the use of a heater 60 affixed by any suitable means (not shown) to a unique junction block 58'. As schematically illustrated, junction block 58' is suitably bored or otherwise machined to receive or provide essentially all, if not all, of the conduit passageways comprising eductive loop 12, as well as to provide for introducing thereto blowback air via conduit 26, and aspirator air via conduit 70, or other suitable motive fluid, and the connection thereto of convective loop 14. Heater 60, which is affixed to junction block 58', is preferably comprised of a stainless steel block 62 provided with convection fins 64 and bored to receive one or more conventional electrical heater cartridges 66 to be supplied with current from a source (not shown).

In the operation of an analyzer of this invention, when wet and dirty gas is to be sampled, such as the combustion product of high sulfur coal, significant quantities of water and sulfuric acid may be expected to be drawn into the analyzer, entrained as vapor in the gaseous product being sampled. Should such normally liquid constituents fall below their dew point in a relatively cooler region of the analyzer they will condense out, thereby permitting the collection of entrained dirt by the liquid condensate and resulting in rapid plugging or blocking of the analyzer channels. To preclude this eventuality, heater 60 is maintained at a temperature of, for example, 500°-600° F. and, accordingly, by conduction and/or convection heats metal junction block 58' and all of the metal tubing in contact with the gas sample to a temperature above the dew point of entrained vapors. Preferably, as shown in dotted line in FIG 5, the analyzer 10 of this invention is also completely enclosed in a cabinet 68 to retain or confine, among other obvious utilities, the heat produced by heater 60 within the cabinet 68.

It will be understood, of course, that it is within the scope of this invention to affix a heater, such as heater 60, to the metal junction block 58 shown in FIGS. 1, 3 and 4 and, by conduction and/or convection, obtain similar benefits to those described above. Moreover, it will be apparent to provide other or similar heater means, in addition to or in lieu of a heater such as heater 60, elsewhere in a cabinet 68 enclosing the analyzer 10 of any of the embodiments of this invention.

Returning to FIG. 5, it will be noted that rotary valve 24' is of a different porting arrangement than rotary valve 24 because of the manner of its placement in junction block 58' relative to blowback air conduit 26 and the channels or conduits comprising eductive loop 12. Notwithstanding, approximately a 90° clockwise rotation of valve 24; as viewed, will blow back the downstream or eductor portion of eductive loop 12, whereas a 90° counterclockwise rotation will blow back the upstream portion of loop 12. It will also be noted that convective loop 14 is located in this upstream portion of loop 12 as opposed to its downstream location relative to valve 12, as shown in FIGS. 1, 2a, 2b and 2c. In addition, it will be noted that convection loop 14 contains a common inlet-outlet junction conduit or chamber 72 where it joins eductive loop 12. The reasons for and advantages of this common junction or diffusion chamber are fully set forth in applicant's copending application, Ser. No. 739,724, now U.S. Pat. No. 4,115,229 filed of even date herewith and entitled "Method And Apparatus For Sampling A Gaseous Stream", the disclosure of which is incorporated herein by reference.

As a general rule, in the practice of this invention, it is preferred that the inlet or probe leg 16 and the outlet or return leg 18 of eductive loop 12 join the chamber or conduit 20 at locations where the pressure head in chamber or conduit 20 is essentially the same or nearly the same; otherwise, it too will render the analyzer 10 somewhat flow sensitive. With particular regard to the orientation of eductive loop 12 and convective loop 14, it may be said that the orientation of eductive loop 12 is of no particular consequence since its flow is forced flow and is controlled by eductor 22. The orientation of convective loop 12, however, is preferably vertical but, in any event, not substantially less than 30° from horizontal. If required by unusual circumstances, it is possible to replace convective loop 12 with a forced flow loop or a forced flow assist and still obtain some of the benefits of this invention. However, it is suggested that serious consideration be given to all possible alternative measures before adapting other than a convective flow loop for sensing device 28, such as one of the illustrated convective flow loops 14.

Accordingly, having hereinabove described the principle, preferred construction and mode of operation of this invention and having illustrated and described what is considered to represent its best embodiments, it should be understood that, within the scope of the appended claims, the invention may be practiced otherwise than as specifically illustrated and described.

I claim:
1. A method for sampling a gaseous fluid in a chamber comprising,
   withdrawing a continuous flow of sample gas along a first loop type flow path extending from said chamber through a flow inducing device and back to said chamber,
   joining inlet and outlet legs of a second loop type flow path at substantially the same location along the length of said first loop type flow path,
   positioning said second loop type flow path upstream of said flow inducing device,
   withdrawing a portion of said sample gas along said second loop type flow path through said inlet leg thereof,
   electrochemically sensing the condition of said gas in said second loop type flow path, and
   returning said sensed gas through said outlet leg of said second loop type flow path to said first loop type flow path upstream of said flow inducing device.
2. A method as in claim 1 which includes withdrawing said gas from said chamber and returning said gas to said chamber at locations of substantially the same pressure head.
3. A method as in claim 1 wherein flow through said second loop type flow path is by convection.
4. A method as in claim 1 wherein the condition of said gas is sensed by measuring its oxygen partial pressure.
5. A method as in claim 1 further including the step of heating said first and second loop type flow paths.

* * * * *